United States Patent
Suzuki et al.

(10) Patent No.: US 7,976,917 B2
(45) Date of Patent: Jul. 12, 2011

(54) MULTI-CHAMBER CONTAINER

(75) Inventors: Toyoaki Suzuki, Tokyo (JP); Koichi Miura, Tokyo (JP); Kenjiro Takayanagi, Yokkaichi (JP)

(73) Assignee: Fujimori Kogyo Co., Ltd., Tokyo (JP)

( * ) Notice: Subject to any disclaimer, the term of this patent is extended or adjusted under 35 U.S.C. 154(b) by 1047 days.

(21) Appl. No.: 10/582,100

(22) PCT Filed: Dec. 10, 2004

(86) PCT No.: PCT/JP2004/018852
§ 371 (c)(1),
(2), (4) Date: Jun. 8, 2006

(87) PCT Pub. No.: WO2005/055918
PCT Pub. Date: Jun. 23, 2005

(65) Prior Publication Data
US 2007/0114144 A1    May 24, 2007

(30) Foreign Application Priority Data
Dec. 11, 2003 (JP) .................. 2003-413200

(51) Int. Cl.
*B29D 22/00* (2006.01)

(52) U.S. Cl. ...................... 428/35.2; 428/35.7
(58) Field of Classification Search .............. 428/35.7, 428/35.2, 35.5; 206/219, 284; 604/48, 82, 604/87, 410
See application file for complete search history.

(56) References Cited

U.S. PATENT DOCUMENTS
| | | | |
|---|---|---|---|
| 4,961,495 A | 10/1990 | Yoshida et al. | |
| 5,683,141 A | 11/1997 | Wakamatsu et al. | |
| 6,287,705 B1 | 9/2001 | Seta et al. | |
| 6,663,940 B1 * | 12/2003 | Osame et al. | ......... 428/141 |

(Continued)

FOREIGN PATENT DOCUMENTS
EP    1394071 A1    3/2004
(Continued)

OTHER PUBLICATIONS
Database WPI Week 200313, Thomson Scientific, London, United Kingdom, XP-002527695.
(Continued)

*Primary Examiner* — Rena L Dye
*Assistant Examiner* — James Yager
(74) *Attorney, Agent, or Firm* — Birch, Stewart, Kolasch & Birch, LLP (57) ABSTRACT

Multi-chamber container (1) having its interior partitioned by weak seal portions (3) provided through detachable heat sealing so that multiple contents are accommodated separately from each other, wherein use is made of heat seal layers consisting of a composition comprising two types of propylene copolymers components (component A and component B) from propylene and ethylene and/or a $C_4$-$C_8$ α-olefin which have the following elution properties. Thus, a region wherein a change of seal strength by a change of heat seal temperature is small has a wide temperature range to thereby facilitate controlling of the seal strength at the weak seal portions. The proportion (mass %) of, to total solution, elution according to the TREF method (temperature: 0 to 140° C. and solvent: ODCB) is as follows. With respect to component A: 15 to 50 at 0° C., and 5 to less than 15 at 60 to 90° C. With respect to component B: 0 to 25 at 0° C., and 15 to 70 at 60 to 90° C.

10 Claims, 3 Drawing Sheets

U.S. PATENT DOCUMENTS

2004/0137177 A1* 7/2004 Saito et al. .................. 428/35.2
2006/0093765 A1* 5/2006 Mueller ....................... 428/35.2

FOREIGN PATENT DOCUMENTS

| JP | 5-5138 U | 1/1993 |
| JP | 8-229100 A | 9/1996 |
| JP | 8-299099 A | 11/1996 |
| JP | 9-99037 A | 4/1997 |
| JP | 2675049 B2 | 7/1997 |
| JP | 2675075 B2 | 7/1997 |
| JP | 2000-219787 A | 8/2000 |
| JP | 2003-52791 A | 2/2003 |
| WO | WO-00/20473 A1 | 4/2000 |
| WO | WO-02/100738 A1 | 12/2002 |

OTHER PUBLICATIONS

Database WPI Week 199725, Thomson Scientific, London, United Kingdom, XP-002527696.
Supplementary European Search Report dated Jun. 8, 2009.
Partial English translation of JP 5-5138 U published on Jan. 26, 1993.

* cited by examiner

MULTI-CHAMBER CONTAINER

TECHNICAL FIELD

The present invention relates to a compartmented container with two or more compartments isolated from each other by a weakly sealed part (separator) which can be broken for internal mixing of contents in individual compartments at the time of their use. The weakly sealed part has a seal strength that can be adjusted easily, and the container also withstands sterilization at 121° C.

BACKGROUND ART

It is common practice in the medical field to use a medicinal container holding plural ingredients separately which are to be mixed immediately before administration. For example, a transfusion solution for IVH (intravenous hyperalimentation), which is composed of carbohydrate, amino acid, and electrolyte as a nutrient source, is stored in a compartmented container holding individual ingredients in separate compartments, thereby protecting glucose and amino acid from deterioration by Maillard reaction, and these ingredients are mixed together immediately before administration.

There are many granted or pending patents (as follows) for the compartmented container with two or more compartments separated from each other which is designed for internal mixing (for example, Patent Document 1: Japanese Patent No. 2675075, Patent Document 2: Japanese Patent No. 2675049, Patent Document 3: Japanese Utility Model Laid-open No. Hei 5-5138, Patent Document 4: Japanese Patent Laid-open No. Hei 8-299099, Patent Document 5: Japanese Patent Laid-open No. Hei 8-229100.) According to these patents, the compartmented container has two or more compartments separated by a weakly sealed part formed therein, so that it permits two or more contents to be mixed in the container without opening the container by rupturing the weakly sealed part by hand or jig (to make compartments join together) at the time of use.

Patent Documents 1 and 2 listed above disclose a compartmented container which is characterized in that the weakly sealed part has a seal layer formed from a mixture of a linear low-density polyethylene resin and a polypropylene resin. Therefore, this seal layer is likely to soften during sterilization at 121° C., resulting in breakage or deformation of the container.

Patent Document 3 listed above discloses a method for producing a compartmented container by inserting in a container a tape (or sheet) capable of weak sealing. This tape is formed from a mixture of polyethylene and polypropylene, and hence it is unsuitable for sterilization at 121° C. as in the case of Patent Documents 1 and 2.

Patent Documents 4 and 5 listed above disclose a compartmented container having a heat-sealable layer formed from a composition of polyethylene and olefin block copolymer or from a composition of polypropylene-based polymer and styrene-based elastomer. These polymer compositions are poor in heat resistance because of a high content of $\alpha$-olefin and elastomer and hence are unsuitable for sterilization at 121° C.

On the other hand, it is also an important factor for containers to perfectly withstand an impact at the time of dropping, for example, to pass the drop test specified in the Food Sanitation Law. The standard of seal strength required for the drop test varies depending on the weight of the content. A container holding 500 mL of liquid, for example, differs from a container holding 1 liter of liquid in heat seal strength required to prevent breakage at the time of dropping. This applies also to the weakly sealed part of a compartmented container.

Therefore, thinking of the weakly sealed part (separator) of a compartmented container, it follows that its seal strength should be comparatively low if the content is less than 500 mL. The weakly sealed part does not need a high seal strength to prevent breakage because the container itself is small. An excessively high seal strength rather makes the weakly sealed part take a long time to break. On the other hand, its seal strength should be comparatively high if the content is 500 mL or more. The weakly sealed part needs a high seal strength because the container is large and the weakly sealed part is subject to a large load at the time of dropping. The weakly sealed part with an excessively low seal strength is likely to break due to the heavy load.

One conventional way to adjust the seal strength of the weakly sealed part of a compartmented container was to change the heat sealing temperature. Unfortunately, the range of change that can be achieved is limited to only about 20° C. (See Patent Document 6: Japanese Patent Laid-open No. 2003-52791.) Thus the conventional technology needs improvement to be able to control the heat seal strength of the weakly sealed part easily and freely in response to the weight of the content in a compartmented container.

There has been a demand for a compartmented container which permits the weakly sealed part to be formed at widely ranged temperatures.

The present invention was completed in view of the foregoing. It is an object of the present invention to provide a compartmented container which withstands sterilization at 121° C. or above without deformation, permits the weakly sealed part to keep its weak seal strength stable even after sterilization, and has good transparency, and which also permits the weakly sealed part to have a seal strength that can be controlled easily and freely.

DISCLOSURE OF INVENTION

In order to achieve the above-mentioned object, the present inventors carried out a series of researches which led to the development of a new compartmented container to hold two or more contents separately in individual compartments. This compartmented container is formed from a resin film or sheet having a heat-sealable layer on at least one side thereof so that the heat-sealable layer constitutes the inner walls of the container. The opposing inner walls are heat-sealed partially and peelably to form the weakly sealed part which divides the inside of the container into compartments. The compartmented container according to the present invention is characterized in that said heat-sealable layer is formed from a composition of propylene copolymer which is obtained by compounding a specific low-crystalline propylene copolymer and a specific high-crystalline propylene copolymer. Owing to this heat-sealable layer, the compartmented container has high heat resistance enough to withstand sterilization at 121° C. and also has good transparency. In addition, the heat-sealable layer shows a wide range of temperature in which the change of seal strength is comparatively small for large change of heat sealing temperature. Because of this property, the weakly sealed part has a seal strength that can be controlled easily and freely.

Therefore, the present invention is directed to a compartmented container defined in the following.

[1] A compartmented container to hold two or more contents separately in individual compartments, which is formed from a resin film or sheet having a heat-sealable layer on at least one side thereof so that the heat-sealable layer constitutes the inner walls of said container, and the opposing inner walls are heat-sealed partially and peelably to form the weakly sealed part which divides the inside of the container into compartments, wherein said heat-sealable layer is formed from a composition of propylene copolymer composed of the following components (A) and (B), wherein Component (A): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 15 wt % and not more than 50 wt %, and the ratio of the amount of elution at 60° C. to 90° C. to the whole amount of elution is not less than 5 wt % and less than 15 wt %, Component (B): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 0 wt % and not more than 25 wt %, and the ratio of the amount of elution at 60° C. to 90° C. to the whole amount of elution is not less than 15 wt % and not more than 70 wt %.

[2] The compartmented container as defined in [1] above, wherein the weakly sealed part is formed by heat-sealing with an easy peel tape inserted between the opposing inner walls, said tape having as the surface layer a heat-sealable layer composed of said composition of propylene copolymer.

[3] The compartmented container as defined in [1] or [2] above, which has a port made from polypropylene resin.

[4] The compartmented container as defined in [1], [2] or [3] above, wherein the composition of propylene copolymers is composed of component (A) and component (B) in a ratio of from 98:2 to 50:50 (by weight).

[5] The compartmented container as defined in any of [1] to [4] above, wherein the composition of propylene copolymers contains a styrene elastomer with a styrene content not more than 25 wt % in a ratio of 1 to 10 wt %.

[6] The compartmented container as defined in any of [1] to [5] above, wherein the resin film or sheet has a laminated structure of at least three layers, including heat-sealable layer, intermediate layer, and the outermost layer.

[7] The compartmented container as defined in any of [1] to [6] above, wherein the resin film or sheet gives a total light transmittance not lower than 80% and a haze value not higher than 25% when tested according to JIS K7105 immediately after sterilization at 121° C. for 30 minutes.

[8] The compartmented container as defined in any of [1] to [7] above, wherein the weakly sealed part gives a heat seal strength of 1 to 6 N/15 mm and the other heat-sealed part than the weakly sealed part gives a heat seal strength not lower than 25 N/15 mm when tested according to JIS Z0238 (for 180° peeling).

[9] The compartmented container as defined in [8] above, wherein the capacity is smaller than 500 mL, and the weakly sealed part has a heat seal strength of 1 to 3 N/15 mm.

[10] The compartmented container defined in [8] above, wherein the capacity is not smaller than 500 mL, and the weakly sealed part has a heat seal strength of 3 to 6 N/15 mm.

The compartmented container according to the present invention withstands sterilization at 121° C. and has good clarity. In addition, it has the weakly sealed part whose seal strength can be adjusted easily and freely according to its capacity. Owing to the optimal and stable seal strength, it excels in drop strength and provides good sealing for the port (through which the content is admitted or discharged).

BEST MODE FOR CARRYING OUT THE INVENTION

Figure 1:
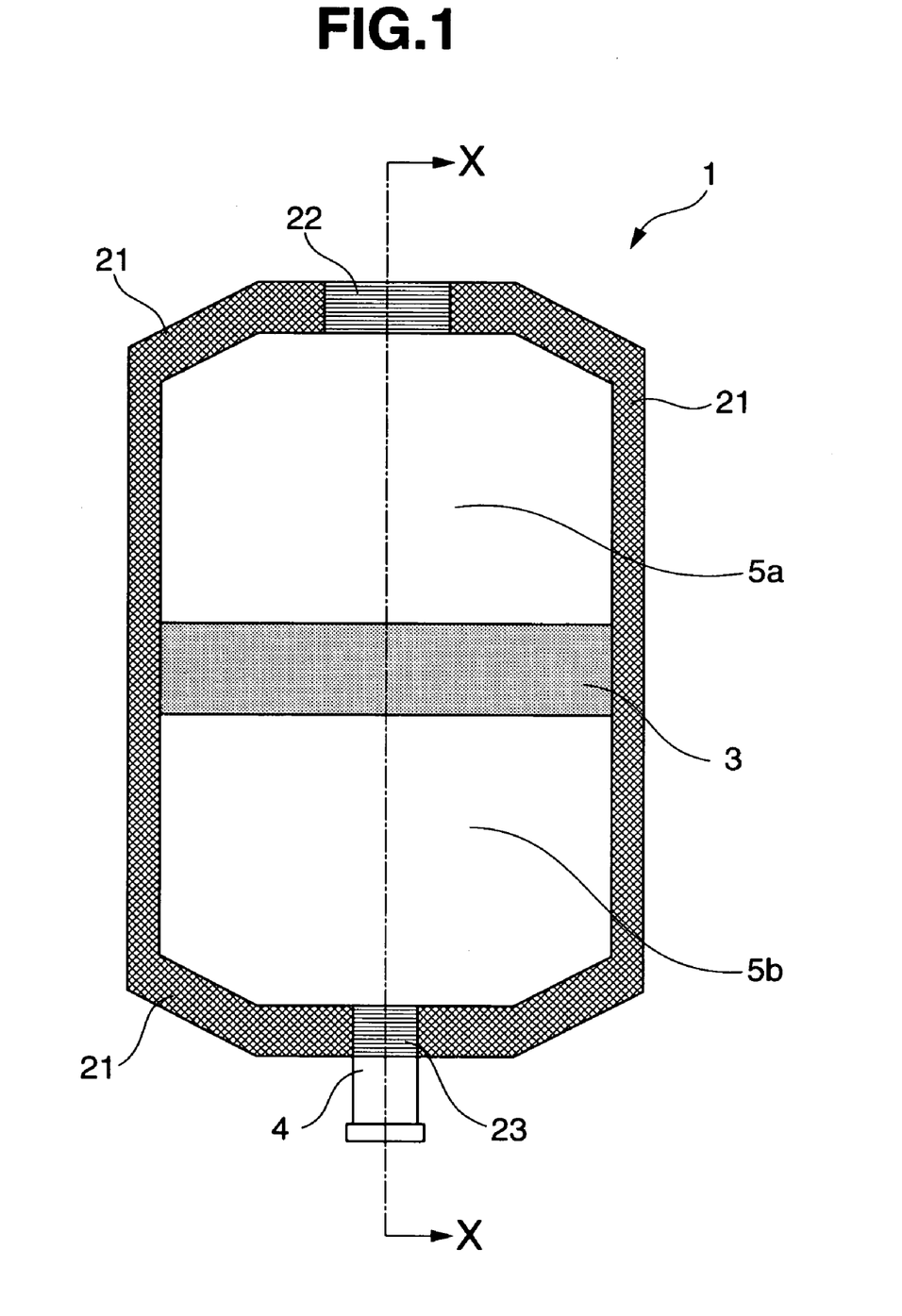
FIG. 1 is a plan view showing an example of the compartmented container according to the present invention.
Figure 2:
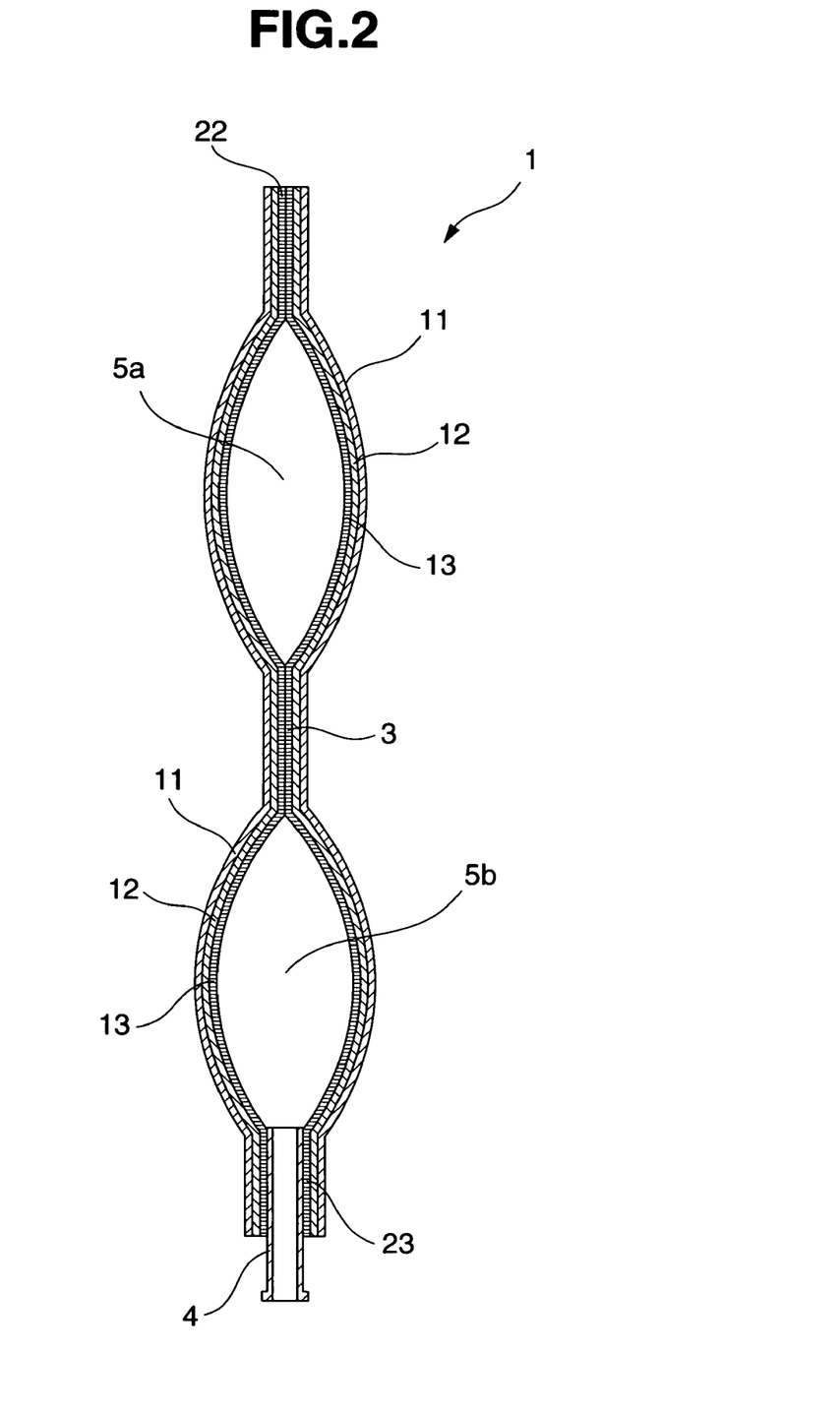
FIG. 2 is a sectional view taken along the line X-X of the compartmented container shown in FIG. 1.
Figure 3:
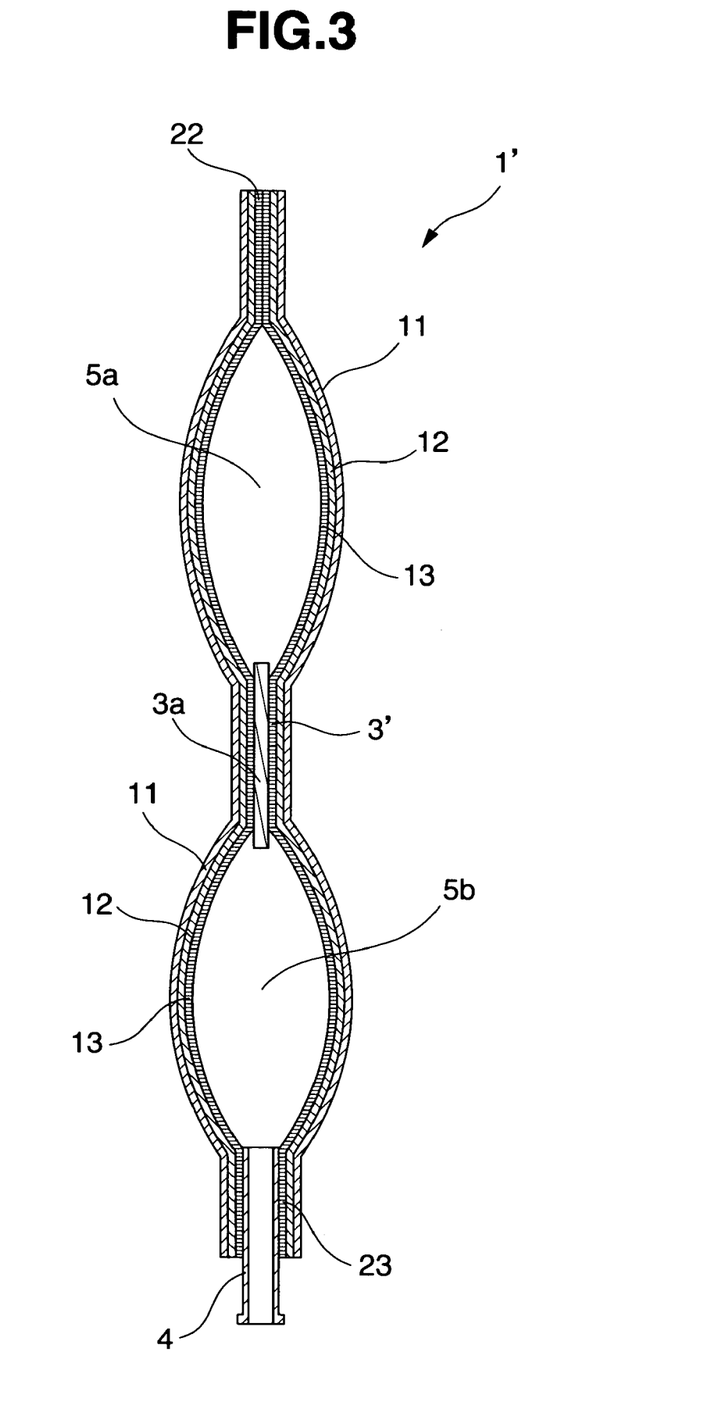
FIG. 3 is a sectional view of another example of the compartmented container according to the present invention.

A detailed description of the invention will be given in the following. FIG. 1 is a plan view showing an example of the compartmented container 1 according to the present invention. FIG. 2 is a sectional view taken along the line X-X of the compartmented container 1 shown in FIG. 1. FIG. 3 is a sectional view of another example of the compartmented container 1' according to the present invention.

The compartmented container 1 shown in FIGS. 1 and 2 is formed from two resin sheets, each having a heat-sealable layer 13 on one side thereof. The heat-sealable layers 13 constitute the inner walls. The resin sheets are strongly sealed to each other along their periphery and are also weakly sealed to each other dividing the inside of the container, so that the strongly sealed part 21 and the weakly sealed part 3 constitute two compartments 5a and 5b. The compartment 5a or 5b is provided appropriately with the port 4 which make it possible that the content is introduced into and discharged from the container. As to the port, it is preferable to use such a port that can be closed after the each compartment has been filled with contents, or can be opened and closed to discharge the content from the container.

It is to be noted in FIGS. 1 and 2 that both side peripheries and upper and lower peripheries of the compartmented container 1 are strongly heat-sealed excluding the central parts of the upper and lower peripheries, so that the strongly sealed part 21 is formed. The central part of the upper periphery is strongly heat-sealed after the filling of content, so that the strongly sealed part 22 is formed. A port 4 is inserted in the central part of the lower periphery, and the center part is strongly heat-sealed with the outer surface of the port 4, so that the strongly sealed part 23 is formed.

The resin sheet constituting the compartmented container 1 consists of three layers, that is, the outermost layer 11, an intermediate layer 12, and the innermost layer 13. The separation of two compartments in the compartmented container 1 is attained by the weakly sealed part 3 which is formed by weakly heat-sealing a part of the opposing innermost layers 13. Rupturing off the weakly sealed part 3 by pressing either of the compartments 5a and 5b attains the connection of both compartments. The weakly sealed part 3' shown in FIG. 3 is also formed by hot-pressing the container from the outside, with an easy-peel tape 3a inserted between the opposing inner walls 13 and 13. This method is preferable.

The above-mentioned method is designed to form the compartmented container 1 by heat-sealing two multi-layered resin sheets piled. However, as regards methods for producing the compartmented container of the present invention, there is another preferred method which consists of preforming a tubular film (of single-layer structure or multi-layer structure) by inflation molding from a synthetic resin and subsequently forming the strongly sealed parts at the upper and lower peripheries of the tube and the weakly sealed part in the middle of the tube and attaching the port to the tube. The resin sheet constituting the compartmented container is not limited to that of three-layer structure. It may be of single-layer structure, two-layer structure, four-layer or more multi-layer structure, depending on the performance required of the compartmented container.

The present invention covers a compartmented container to hold two or more contents separately in individual compartments, which is formed from a resin film or sheet having a heat-sealable layer on at least one side thereof so that the heat-sealable layer constitutes the inner walls of said container, and the opposing inner walls are heat-sealed partially and peelably to form the weakly sealed part which divides the inside of the container into compartments, wherein said heat-sealable layer is formed from a composition of propylene copolymer composed of the following components (A) and (B), wherein Component (A): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 15 wt % and not more than 50 wt %, and the ratio of the amount of elution at 60° C. to 90° C. to the whole amount of elution is not less than 5 wt % and less than 15 wt %, Component (B): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 0 wt % and not more than 25 wt %, and the ratio of the amount of elution at 60° C. to 90° C. to the whole amount of elution is not less than 15 wt % and not more than 70 wt %.

Here, the temperature rising elution fractionation method (TREF) is a known method for analyzing the distribution of polymer constituents. It is based on the principle that individual polymer constituents vary in crystalline structure and hence vary in the rate of dissolution in or precipitation from solvent. According to this method, a polymer sample is completely dissolved in a solvent at a high temperature and the resulting solution is slowly cooled in the presence of an inert carrier. During cooling, high crystalline polymer constituents (which readily crystallize) precipitate first on the surface of the inert carrier, thereby forming a polymer layer and low crystalline or amorphous polymer constituents (which hardly crystallize) precipitate next to form another polymer layer. After the polymer layers have been formed, the temperature is raised continuously or stepwise. During heating, low crystalline or amorphous polymer constituents elute first and high crystalline polymer constituents elute next. Therefore, it becomes possible to analyze the distribution of polymer constituents by the elusion curve that the amounts of elution at the temperature changed draw. In the present invention, the TREF method is practiced by using o-dichlorobenzene as the solvent and changing the temperature in the range of 0° C. to 140° C.

According to the present invention, the component (A) should have the distribution of polymer constituents such that the ratio of the amount of elution at 0° C. to the whole amount of elution is not less than 15 wt % (preferably not less than 18 wt %) and not more than 50 wt % (preferably not more than 40 wt %). With a smaller ratio of the amount of elution than specified above, the composition of propylene copolymer hardly has a range of the temperature in which seal strength changes small despite large variation of heat-sealing temperature. The compartmented container formed from such a composition of propylene copolymer is hard to control its seal strength, and is poor in flexibility, and is stiff to the touch, and tends to show small drop strength. Thus it does not produce the effect intended by the present invention. By contrast, with a larger ratio of the amount of elution than specified above, the composition of propylene copolymer may cause blocking of the inner walls of the compartmented container during sterilization at 121° C.

In addition, the component (A) should have the distribution of polymer constituents such that the ratio of the amount of elution at 60° C. to 90° C. to the whole amount of elution is not less than 5 wt % (preferably not less than 6 wt %) and less than 15 wt % (preferably not more than 10 wt %) With a smaller ratio of the amount of elution than specified above, the composition of propylene copolymer is poor in transparency. By contrast, with a larger ratio of the amount of elution than specified above, the composition of propylene copolymer is poor in heat resistance and the compartmented container will deform during sterilization at 121° C.

According to the present invention, the component (B) should have the distribution of polymer constituents such that the ratio of the amount of elution at 0° C. to the whole amount of elution is not less than 0 wt % (preferably not less than 2 wt %) and not more than 25 wt % (preferably not more than 15 wt %). With a larger ratio of the amount of elution than specified above, the composition of propylene copolymer may cause blocking of the inner walls of the compartmented container during sterilization at 121° C., making it difficult to discharge the contents.

In addition, the component (B) should have the distribution of polymer constituents such that the ratio of the amount of elution at 60° C. to 90° C. to the whole amount of elution is not less than 15 wt % (preferably not less than 20 wt %) and not more than 70 wt % (preferably not more than 60 wt %). With a smaller ratio of the amount of elution than specified above, the composition of propylene copolymer presents difficulties of stable heat-sealing for the weakly sealed part. By contrast, with a larger ratio of the amount of elution than specified above, the composition of propylene copolymer is poor in heat resistance and the compartmented container has a tendency to deform during sterilization at 121° C. and presents difficulties of stable heat-sealing for the weakly sealed part.

According to the present invention, the composition of propylene copolymer is composed of the components (A) and (B) as mentioned above. The component (A) has a narrow range of heat-sealing temperature (about 20° C.) that controls the seal strength of the weakly sealed part; however, it has superior properties in fusion bonding between films. The component (B) is highly flexible and contributes to heat resistance and drop strength. The combination of the components (A) and (B) has properties to extend the range of heat-sealing temperature to 25° C. for the weakly sealed part and also improves the strength of fusion bonding between the film and the port. The ratio of the component (A) to the component (B) is usually from 98:2 to 50:50 (by weight), preferably from 95:5 to 60:40 (by weight). With a ratio outside the range specified above, the composition of propylene copolymer will hardly have a range of the temperature in which seal strength changes small despite large variation of heat-sealing temperature. This may hinder the effect of the present invention.

Each of the components (A) and (B) constituting the composition of propylene copolymer is a propylene copolymer composed of propylene and ethylene and/or $C_{4-8}$ α-olefin.

Here, the $C_{4-8}$ α-olefin mentioned above includes, for example, butene-1,3-methylbutene-1, pentene-1,4-methylpentene-1, hexene-1, and octene-1. They may be used alone or in combination with one another.

To be concrete, the propylene copolymer in the present invention should preferably be a copolymer of propylene and ethylene or a copolymer of propylene and $C_{4-8}$ α-olefin. The $C_{4-8}$ α-olefin should preferably be butene-1.

According to the present invention, the components (A) and (B) as the constituents of the composition of propylene copolymer are not specifically restricted so long as they have the elusion ratio mentioned above that is determined by the TREF test (using o-dichlorobenzene as the solvent) at 0° C. and from 60 to 90° C. in the range of temperature from 0° C. to 140° C. Moreover, they may also be prepared by various methods.

The components (A) and (B), as the constituents of the composition of propylene copolymer, may be produced by the following method, for example, three methods (1) to (3).
(1) Stepwise polymerization involving at least two steps. Polymerization in the first step is intended to produce a propylene homopolymer or a random copolymer of propylene and a small amount of ethylene and/or $C_{4-8}$ α-olefin. Polymerization in the second or farther step is intended to produce a copolymer of propylene and a small amount of ethylene and/or $C_{4-8}$ α-olefin in the presence of the polymer which has been produced in the preceding step.
(2) Blending of a propylene homopolymer or a random copolymer of propylene and a small amount of ethylene and/or $C_{4-8}$ α-olefin with a random copolymer of ethylene and a small amount of ethylene and/or $C_{4-8}$ α-olefin.
(3) Blending of a propylene homopolymer or a random copolymer of propylene and a small amount of ethylene and/or $C_{4-8}$ α-olefin with a random copolymer of ethylene and/or $C_{4-8}$ α-olefin and propylene. Of these three methods, the first one is most desirable from the economical point of view.

The method (1) for stepwise polymerization may employ any catalyst which is not specifically restricted. A preferred catalyst is one which is composed of an organoaluminum compound and a solid component essentially containing titanium atoms, magnesium atoms, halogen atoms, and an electron donor compound.

The organoaluminum compound mentioned above may be a compound represented by $R^1{}_m AlX_{(3-m)}$, where $R^1$ denotes a $C_{1-12}$ hydrocarbon residue, X denotes a halogen atom, and m denotes a number of 1 to 3. Examples of the organoaluminum compound include trialkylaluminum halide (such as trimethylaluminum chloride and trimethylaluminum chloride), dialkylaluminum halide (such as dimethylaluminum chloride and diethylaluminum chloride), alkylaluminum sesquihalide (such as methylaluminum sesquichloride and ethylaluminum sesquichloride), and alkylaluminum hydride (such as diethylaluminum hydride).

The solid component essentially containing titanium atoms, magnesium atoms, halogen atoms, and an electron donor compound may be any known one which is used for the stepwise polymerization. Titanium atoms may be supplied from a titanium compound represented by $Ti(OR^2)_{(4-n)}X_n$, where $R^2$ denotes a $C_{1-10}$ hydrocarbon residue, X denotes a halogen atom, and n denotes a number of 0 to 4. Preferred titanium compounds are titanium tetrachloride, tetraethoxy titanium, and tetrabutoxy titanium.

Magnesium atoms may be supplied from a magnesium compound such as dialkyl magnesium, magnesium dihalide, dialkoxy magnesium, and alkoxymagnesium halide. Of these compounds, magnesium dihalide is preferable. Halogen atoms include fluorine, chlorine, bromine, and iodine. Of these halogen atoms, chlorine is preferable. Halogen atoms are usually supplied from the above-mentioned titanium compound or magnesium compound; however, they may also be supplied from such halides as aluminum halide, silicon halide, and tungsten halide.

The electron donor compound may be selected from oxygen-containing compounds (such as alcohols, phenols, ketones, aldehydes, carboxylic acids, organic or inorganic acids, and derivatives thereof) and nitrogen-containing compounds (such as ammonia, amines, nitriles, and isocyanates). Of these compounds, inorganic acid esters, organic acid esters, and organic acid halides are preferable. Silicate ester, phthalate ester, acetate cellosolve ester, and phthalic halide are particularly preferable.

The silicate ester is an organosilicon compound represented by $R^3R^4{}_{(3-p)}Si(OR^5)_p$, where $R^3$ denotes a $C_{3-20}$ (preferably $C_{4-10}$) branched aliphatic hydrocarbon residue or a $C_{5-20}$ (preferably $C_{6-10}$) alicyclic hydrocarbon residue, $R^4$ denotes a $C_{1-20}$ (preferably $C_{1-10}$) branched or linear aliphatic hydrocarbon residue, $R_5$ denotes a $C_{1-10}$ (preferably $C_{1-4}$) aliphatic hydrocarbon residue, and p denotes a number of 1 to 3. Examples of the organosilicon compound include t-butyl-methyl-dimethoxysilane, t-butyl-methyl-diethoxysilane, cyclohexyl-methyl-dimethoxysilane, and cyclohexyl-methyl-diethoxysilane.

The method (1) for producing the components (A) and (B) as the constituents of the composition of propylene copolymer may be practiced as follows. In the first step, the polymerization reactor is supplied with propylene alone or together with a small amount of ethylene and/or $C_{4-8}$ α-olefin and polymerization is carried out in the presence of the catalyst mentioned above at a polymerization temperature of 50 to 150° C. (preferably 50 to 100° C.) and at a propylene partial pressure of 0.5 to 4.5 MPa (preferably 1.0 to 3.5 MPa). In the second stage, the polymerization reactor is supplied with propylene and ethylene and/or $C_{4-8}$ α-olefin in the presence of the polymer obtained in the first step and polymerization is carried out in the presence of the catalyst mentioned above at a polymerization temperature of 50 to 150° C. (preferably 50 to 100° C.), with the partial pressures of propylene and ethylene and/or $C_{4-8}$ α-olefin adjusted to 0.3 to 4.5 MPa (preferably 0.5 to 3.5 MPa).

Incidentally, polymerization may be accomplished by a batchwise method, a continuation method, or a semi-batchwise method; however, it is desirable that polymerization in the first and second steps be carried out in gas phase or liquid phase, with the residence time in each step adjusted to 0.5 to 10 hours (preferably 1 to 5 hours). The above-mentioned process may yield the composition of propylene copolymer in the form of sticky powder. This problem may be solved by adding an active hydrogen-containing compound to the polymerization reactor after the first step polymerization, before the second step polymerization, or during the second step polymerization. The amount of the active hydrogen-containing compound should be 100 to 1000 times (in mole) the amount of titanium atoms in the solid component of the catalyst and 2 to 5 times (in mole) the amount of the organoaluminum compound of the catalyst. Examples of the active hydrogen-containing compound include water, alcohols, phenols, aldehydes, carboxylic acids, acid amides, ammonia, and amines.

According to the present invention, the composition of propylene copolymer is composed of the components (A) and (B), which are so prepared as to have a specific elusion ratio determined by the TREF test (using o-dichlorobenzene as the solvent) at 0° C. and from 60 to 90° C. in the range of temperature from 0° C. to 140° C., as mentioned above. This requirement is met by the multi-step copolymerization of propylene with ethylene and/or $C_{4-8}$ α-olefin which yields a propylene copolymer having adequately controlled crystallinity, or by properly selecting a catalyst that controls the stereoregularity of propylene copolymer.

The composition of propylene copolymer composed of the components (A) and (B) mentioned above may be incorporated with a styrene elastomer (not more than 25 wt %) so that it has a broader range of heat-sealing temperature for an adequate weak seal strength. The ratio of the amount of the styrene elastomer in the composition of propylene copolymer is not less than 1 wt %, preferably not less than 5 wt %, and not more than 10 wt %, preferably not more than 8 wt %. When the ratio of the amount of the styrene elastomer in the composition of propylene copolymer is less than 1 wt %, the effect of broadening the heat-sealing temperature for an adequate weak seal strength may not come out. When the ratio of the amount of the styrene elastomer is more than 10 wt %, the composition of propylene copolymer may cause blocking of the inner walls of the compartmented container.

The composition of propylene copolymer according to the present invention may be incorporated with various known additives, such as antioxidant, light absorber, neutralizer, α-crystal nucleating agent, β-crystal nucleating agent, antiblocking agent, and slip agent, in an amount not harmful to the effect of the present invention.

The ratio of the component (A) to the component (B) should be from 98:2 to 50:50 (by weight), preferably from 90:10 to 60:40 (by weight). When the component (A) is more than specified above and the component (B) is less than specified above, the composition of propylene copolymer tends to bring difficulties of stable heat sealing for the weakly sealed part. When the component (A) is less than specified above and the component (B) is more than specified above, the composition of propylene copolymer tends to bring difficulties of stable heat sealing for the weakly sealed part and good sealing with the port when the container is completed.

The compartmented container according to the present invention is formed from a resin film or sheet having a heat-sealable layer on at least one side thereof. It should preferably be comprised of at least three layers that is, a heat-sealable layer, an intermediate layer, and an outermost layer, from the standpoint of ability to withstand sterilization at 121° C., sufficient drop strength, and good handling properties.

The intermediate layer and the outermost layer are not specifically restricted in the compositions from which they are made. Some examples of the compositions are listed in (w) to (z) below.

(w) The outermost layer is formed from a composition of propylene copolymer which is composed of the component (A) and a propylene homopolymer in a ratio of from 5:95 to 95:5 (by weight), and the intermediate layer is formed from a composition of the component (A) and a metallocene plastomer having a tensile modulus not higher than 200 MPa in a ratio of from 95:5 to 70:40 (by weight). The metallocene plastomer having a tensile modulus lower than 200 MPa is commercially available, for example, under a trade name of "Kernel" from Japan Polychem. "Metallocene plastomer having a tensile modulus not higher than 200 MPa" in the following is defined as above. Incidentally, the tensile modulus is measured according to JIS K7127.

(x) The outermost layer is formed from a composition composed of the component (A) (5 to 90 pbw), the component (B) (5 to 90 pbw), and propylene homopolymer (5 to 90 pbw). The intermediate layer is formed from a composition composed of the component (A) (5 to 90 pbw), the component (B) (5 to 90 pbw), and the metallocene plastomer having a tensile modulus not higher than 200 MPa (5 to 40 pbw).

(y) The outermost layer is formed from a composition composed of the component (A) and a propylene homopolymer in a ratio of from 5:95 to 95:5 (by weight), and the intermediate layer is formed from a composition composed of the component (A) and a thermoplastic elastomer in a ratio of from 95:5 to 70:40 (by weight). The thermoplastic elastomer includes ethylene propylene elastomer (which is commercially available under a trade name of "Tafmer" from Mitsui Chemicals, Inc.) and styrene elastomer (which is commercially available under a trade name of "Dynaron" from JSR Corporation). "Thermoplastic elastomer" in the following is defined as above.

(z) The outermost layer is formed from a composition composed of the component (A) (5 to 90 pbw), the component (B) (5 to 90 pbw), and propylene homopolymer (5 to 90 pbw). The intermediate layer is formed from a composition composed of the component (A) (5 to 90 pbw), the component (B) (5 to 90 pbw), and the thermoplastic elastomer (5 to 40 pbw).

Of the above-mentioned compositions (w) to (z), it is preferable that the outermost layer is formed from a composition composed of the component (A) and a propylene homopolymer in a ratio of from 5:95 to 95:5 (by weight), or from a composition composed of the component (A) (5 to 90 pbw), the component (B) (5 to 90 pbw), and a polypropylene homopolymer (5 to 90 pbw). The resin film or sheet gives the compartmented container which has improved heat resistance of surface thereof and is free of sticking feel and superior in bag-making performance and printability.

Of the above-mentioned compositions (w) to (z), it is preferable that the intermediate layer is formed from a composition composed of the component (A) and a metallocene plastomer having a tensile modulus equal to or lower than 200 MPa in a ratio of from 95:5 to 70:40 (by weight), or from a composition composed of the component (A) (5 to 90 pbw), the component (B) (5 to 90 pbw), and a metallocene plastomer having a tensile modulus lower than 200 MPa (5 to 40 pbw). The resin film or sheet gives the compartmented container which exhibits good transparency and flexibility after sterilization at 121° C. and excels in drop impact strength.

Of the above-mentioned compositions (w) to (z), it is preferable that the intermediate layer is formed from a composition composed of the component (A) and a thermoplastic elastomer in a ratio of from 95:5 to 70:40 (by weight), or from a composition composed of the component (A) (5 to 90 pbw), the component (B) (5 to 90 pbw), and a thermoplastic elastomer (5 to 40 pbw). (The thermoplastic elastomer should preferably be a styrene-based elastomer containing equal to or less than 20% of styrene.) The resin film or sheet gives the compartmented container which exhibits good transparency and flexibility after sterilization at 121° C. and excels in drop impact strength.

Incidentally, the metallocene plastomer having a tensile modulus equal to or lower than 200 MPa should preferably be one which has a melt flow rate of 0.5 to 10 g/10 min at 190°

C. and a density of 0.87 to 0.94 g/cm³ from the standpoint of good heat resistance and flexibility.

Also, the thermoplastic elastomer should preferably be a styrene-based elastomer containing equal to or less than 25 wt % of styrene from the standpoint of good clarity and after sterilization at 121° C.

The resin film or sheet in the present invention, which has a three-layer or more multi-layer structure, may be formed by lamination in any manner without specific restrictions. Adequate methods for lamination include dry lamination, extrusion lamination, and multi-layer coextrusion.

In the present invention, the heat-sealing layer constituting the inner walls of the compartmented container is formed from a composition composed of the components (A) and (B). Because of this structure of the heat-sealing layer, the compartmented container can withstand sterilization at 121° C., retain the weak seal strength stable, and keep good trasperency without deformation even after sterilization at 121° C. Moreover, the heat-sealing layer provides a wide range of the temperature in which seal strength changes small despite large variation of heat-sealing temperature. This facilitates control of seal strength in the weakly sealed part. Therefore, the compartmented container according to the present invention has an optimal and stable seal strength depending on the capacity of the container and excels in drop impact strength and seal strength at the port.

To control the seal strength of the weakly sealed part in a proper range easily and freely, when taking the safety factor into consideration, the condition of the temperature to form heat sealing for the weakly sealed part desirably should keep a margin of 25° C. or more, particularly from 30° C. to 40° C. The margin means the difference between the lowest and highest temperatures at which the weakly sealed part with a seal strength explained as follows can be formed.

It is possible to make the weakly sealed part that withstands sterilization at 121° C. from the component (A) alone when forming the compartmented container. In this case, however, the heat-sealable layer cannot keep such a broad margin of heat sealing temperature. Only the present invention having the heat-sealable layer composed of the components (A) and (B) makes it possible to give the weakly sealed part an aptitude for withstanding sterilization at 121° C. and to keep a broad margin of the temperatures such as 25° C. or more when forming the weakly sealed part. The heat-sealable layer as mentioned above can firmly seal the port to the compartmented container at a low heat-sealing temperature. This eliminates heat sealing at an excessively high temperature, thereby preventing the content from leaking from the container, and keeping stable seal with the port.

According to the present invention, the proportion of the total amount of the components (A) and (B) to the composition of propylene copolymer constituting the heat-sealable layer should be 50 wt % or more, preferably not less than 70 wt %, more preferably not less than 90 wt %. With the amount less than specified above, the heat-sealable layer has a narrow range of heat sealing temperature and may give the weakly sealed part an undesired weak seal strength.

The term "weakly sealed part" as used in the present invention means a heat-sealed part that can be opened when necessary. The seal strength is not specifically restricted. A preferable seal strength is 1 to 6 N/15 mm, which is measured according to JIS Z0238 (for peel strength at 180°).

The conditions for realizing such a weakly sealed part that has the desired heat seal strength are determined properly by the consideration of the constitution of the materials and the thickness of the resin film or sheet having the heat-sealable layer on at least one side thereof. The heat-sealable layer permits heat sealing under the following conditions as demonstrated in Examples that follow.

Sealing pressure: 0.2 MPa
Sealing time: 2 seconds
Sealing temperature: 145 to 1802 C.

In this case, the margin of the heat-sealing temperature for the weakly sealed part can be 25° C. or more. And this means that the heat seal strength of the weakly sealed part can be controlled easily and freely because it gradually increases in proportion to the heat-sealing temperature.

Incidentally, the condition for forming the weakly sealed part can adopt the sealing pressure from 0.1 to 0.6 MPa and the sealing time from 1 to 8 seconds.

As mentioned above, the easy and free control of the heat seal strength of the weakly sealed part makes the compartmented container according to the present invention enable to set an adequate seal strength in response to the weight and volume of the contents. So, it is possible to control the weakly sealed part set in a range of the most suitable heat seal strength according to the volume and weight of the contents. For example, the seal strength of the weakly sealed part can be adjusted easily to 1 to 3 N/15 mm when the capacity is less than 500 mL, and 3 to 6 N/15 mm when not less than 500 mL, respectively. When a container has a whole volume smaller than 500 mL of the contents and a seal strength larger than 3 N/15 mm, it gives trouble to break-open the weakly sealed part by pressing the container, and also may break in other parts than the weakly sealed part. When a container has a whole volume not smaller than 500 mL of the contents and a seal strength smaller than 3 N/15 mm, the weakly sealed part may break during transportation or at the time of dropping.

For the compartmented container of the present invention to have a broad range of capacity, it is desirable that the weakly sealed part has a seal strength of 1 to 6 N/15 mm, and the strongly sealed part in the periphery of the container has a seal strength equal to or larger than 20 N/15 mm, preferably equal to or larger than 25 N/15 mm.

The conditions for realizing the strongly sealed part are determined by the consideration of the constitution of the materials and the thickness of the resin film or sheet used. For example, typical conditions allow a sealing temperature of 200° C., (a sealing pressure of 0.2 MPa, and a sealing time of 2 seconds). The strongly sealed part usually does not need more stringent sealing conditions than the weakly sealed part. It is only necessary to set the sealing temperature at 200° C. or above, preferably 210° C. or above, while keeping other conditions such as sealing pressure and time as usual. A sealing pressure of 0.1 to 0.6 MPa and a sealing time of 0.5 to 8 seconds will be adequate to form the strongly sealed part.

Heat sealing in the present invention may be accomplished by common heat-sealing method, which is designed to sandwich and press the desired part to be sealed with a pair of heating elements heated to a prescribed temperature or by any other known heat-sealing methods such as impulse heat sealing and high-frequency sealing which induces heat in the heat seal layers to be sealed.

The weakly sealed part may also be formed by heat-sealing with an easy peel tape inserted between the opposing inner walls of the container. The easy peel tape has a heat-sealable layer as a surface layer made from the composition of propylene copolymer mentioned above. Inserting the easy peel tape has a defect of an additional step complicating the sealing process but brings a possibility of the simplification of the administration of the sealing process providing a stable heat-sealed area. For example, an easy peel tape having one side of propylene homopolymer and the other side of propylene copolymer makes it possible to form both the weakly sealed part and the strongly sealed part under the same conditions. An easy peel tape having both sides formed from the composition of the propylene copolymer mentioned above makes it possible to control the seal strength of the weakly sealed part in the same way as mentioned above.

It is preferable that the resin film or sheet of the compartmented container according to the present invention has a total light transmittance of 80% or above, a haze value of 25% or below, and a tensile modulus of 400 MPa or below immediately after sterilization at 121° C. for 30 minutes. Incidentally, "total light transmittance" and "haze value" are measured according to JIS K7105 and "tensile modulus" is measured according to JIS K7127.

EXAMPLES

The invention will be described in more detail with reference to the following Examples and Comparative Examples, which are not intended to restrict the scope thereof.

Example 1

A sheet 1 with a total thickness of 200 μm, which consists of a surface layer with a thickness of 20 μm, an intermediate layer with a thickness of 140 μm, and a heat-sealable layer with a thickness of 40 μm, was prepared by multi-layer coextrusion from the following materials.

Material for the surface layer: A composition composed of component (a) defined below and propylene homopolymer in a ratio of 9:1.

Material for the intermediate layer: A composition composed of component (a) defined below and metallocene plastomer ("Kernel" from Japan Polychems, Inc.) having a tensile modulus of 100 MPa in a ratio of 8:2.

Material for the heat-sealable layer: A composition composed of component (a) defined below and component (b) defined below in a ratio of 6:4.

[Component (a)]

A reactor-type propylene-based TPO (Thermoplastic Olefin Elastomer) (from Mitsubishi Chemical Corporation), which gives such a specific ratio of the amount of elution measured by the temperature rising elution fractionation method at temperatures ranging from 0° C. to 140° C. with o-dichlorobenzene as a solvent that the ratio of the amount of elution at 0° C. to the whole amount of elution is 23 wt %, and the ratio of the amount of elution at 60° C. to 90° C. to the whole amount of elution is 8 wt %.

[Component (b)]

A reactor-type propylene-based TPO (Thermoplastic Olefin Elastomer) (from Mitsubishi Chemical Corporation), which gives such a specific ratio of the amount of elution measured by the temperature rising elution fractionation method at temperatures ranging from 0° C. to 140° C. with o-dichlorobenzene as a solvent that the ratio of the amount of elution at 0° C. to the whole amount of elution is 7 wt %, and the ratio of the amount of elution at 60° C. to 90° C. to the whole amount of elution is 50 wt %.

The thus obtained sheet 1 was heat-sealed at 200° C. and 0.5 MPa for 4 seconds to form the peripheral sealed part and the port sealed part. Then it was heat-sealed at 160° C. and 0.2 MPa for 2 seconds to form the weakly sealed part that separates the inside of the container into two compartments. Thus there was obtained a compartmented container 1. It was found that the peripheral sealed part and the weakly sealed part of the compartmented container 1 have a seal strength of 35 N/15 mm and 3.2 N/15 mm, respectively. Several weakly sealed parts were formed under the conditions that only heat-sealing temperature was varied so that they gave a seal strength of 1 to 6 N/15 mm. The heat-sealing temperature ranged from 145° C. to 180° C. as shown in Table 1 below. This result indicates that the weakly sealed parts allow a margin of 35° C. for their heat-sealing temperature.

TABLE 1

| Sealing temperature (° C.) | Seal strength (N/15 mm)* |
| --- | --- |
| 145 | 1 |
| 155 | 2.5 |
| 165 | 4 |
| 175 | 5 |
| 180 | 6 |

*Measured based on JIS Z0238 (in terms of 180° peel strength) for samples sealed at 0.2 MPa for 2 seconds. In Examples 1 to 6, any sealed part having a seal strength not higher than 6 N/15 mm is regarded as the weakly sealed part.

The resulting compartmented container 1 having two compartments divided was evaluated as follows. Each of two compartments was filled with 1 liter of distilled water for injection and then sealed. The container underwent sterilization at 121° C. for 30 minutes. The weakly sealed part did not rupture after sterilization, and it was possible to join the compartments together easily by pressing with hand. The container was found to have a total light transmittance of 90%, a haze value of 13%, and a tensile modulus of 220 Mpa, which were measured immediately after sterilization at 121° C. for 30 minutes.

Example 2

A sheet 2 with a total thickness of 200 μm, which consists of a surface layer with a thickness of 20 μm, an intermediate layer with a thickness of 140 μm, and a heat-sealable layer with a thickness of 40 μm, was prepared by multi-layer coextrusion from the following materials.

Material for the surface layer: A composition composed of component (a) defined above and propylene homopolymer in a ratio of 9:1.

Material for the intermediate layer: A composition composed of component (a) defined above and a styrene-based elastomer containing 20% styrene ("Hybrar" from Kuraray Co., Ltd.) in a ratio of 9:1.

Material for the heat-sealable layer: A composition composed of component (a) defined above and component (b) defined above in a ratio of 7:3.

The thus obtained sheet 2 was heat-sealed at 200° C. and 0.5 MPa for 4 seconds to form the peripheral sealed part and the port sealed part. Then it was heat-sealed at 160° C. and 0.2 MPa for 2 seconds to form the weakly sealed part that separates the inside of the container into two compartments. Thus there was obtained a compartmented container 2. It was found that the peripheral sealed part and the weakly sealed part of the compartmented container 2 have a seal strength of 34 N/15 mm and 3.5 N/15 mm, respectively. It was found that the weakly sealed part allows a margin of 30° C. for its heat-sealing temperature, which was measured in the same way as in Example 1.

The resulting compartmented container 2 having two compartments divided was evaluated as follows. Each of two compartments was filled with 1 liter of distilled water for injection and then sealed. The container underwent sterilization at 121° C. for 30 minutes. The weakly sealed part did not rupture after sterilization, and it was possible to join the compartments together easily by pressing with hand. The container was found to have a total light transmittance of 90%, a haze value of 15%, and a tensile modulus of 200 Mpa, which were measured immediately after sterilization at 121° C. for 30 minutes.

Example 3

A sheet 3 with a total thickness of 250 μm, which consists of a surface layer with a thickness of 20 μm, an intermediate layer with a thickness of 180 μm, and a heat-sealable layer with a thickness of 50 μm, was prepared by multi-layer coextrusion from the following materials.
  Material for the surface layer: A composition composed of component (a) defined above, component (b) defined above, and propylene homopolymer in a ratio of 8:1:1.
  Material for the intermediate layer: A composition composed of component (a) defined above, component (b) defined above, and a metallocene plastomer ("Kernel" from Japan Polychems, Inc.) having a tensile modulus of 80 MPa in a ratio of 6:2:2.
  Material for the heat-sealable layer: A composition composed of component (a) defined above and component (b) defined above in a ratio of 7:3.

The thus obtained sheet 3 was heat-sealed at 210° C. and 0.5 MPa for 4 seconds to form the peripheral sealed part and the port sealed part. Then it was heat-sealed at 170° C. and 0.2 MPa for 2 seconds to form the weakly sealed part that separates the inside of the container into two compartments. Thus there was obtained a compartmented container 3. It was found that the peripheral sealed part and the weakly sealed part of the compartmented container 3 have a seal strength of 30 N/15 mm and 4.2 N/15 mm, respectively. It was found that the weakly sealed part allows a margin of 30° C. for its heat-sealing temperature, which was measured in the same way as in Example 1.

The resulting compartmented container 3 having two compartments divided was evaluated as follows. Each of two compartments was filled with 1 liter of distilled water for injection and then sealed. The container underwent sterilization at 121° C. for 30 minutes. The weakly sealed part did not rupture after sterilization but it was possible to join the compartments together easily by pressing with hand. The container was found to have a total light transmittance of 90%, a haze value of 14%, and a tensile modulus of 200 Mpa, which were measured immediately after sterilization at 121° C. for 30 minutes.

Example 4

A sheet 4 with a total thickness of 200 μm, which consists of a surface layer with a thickness of 20 μm, an intermediate layer with a thickness of 140 μm, and a heat-sealable layer with a thickness of 40 μm, was prepared by multi-layer coextrusion from the following materials.
  Material for the surface layer: A composition composed of component (a) defined above, component (b) defined above, and propylene homopolymer in a ratio of 8:1:1.
  Material for the intermediate layer: A composition composed of component (a) defined above, component (b) defined above, and a styrene-based elastomer containing 20% styrene ("Hybrar" from Kuraray Co., Ltd.) in a ratio of 7:2:1.
  Material for the heat-sealable layer: A composition composed of component (a) defined above and component (b) defined above in a ratio of 7:3.

The thus obtained sheet 4 was heat-sealed at 200° C. and 0.5 MPa for 3 seconds to form the peripheral sealed part and the port sealed part. Then it was heat-sealed at 160° C. and 0.2 MPa for 2 seconds to form the weakly sealed part that separates the inside of the container into two compartments. Thus there was obtained a compartmented container 4. It was found that the peripheral sealed part and the weakly sealed part of the compartmented container 4 have a seal strength of 35 N/15 mm and 3.5 N/15 mm, respectively. It was found that the weakly sealed part allows a margin of 35° C. for its heat-sealing temperature, which was measured in the same way as in Example 1.

The resulting compartmented container 4 having two compartment divided was evaluated as follows. Each of two compartments was filled with 1 liter of distilled water for injection and then sealed. The container underwent sterilization at 121° C. for 30 minutes. The weakly sealed part did not rupture after sterilization, and it was possible to join the compartments together by pressing with hand. The container was found to have a total light transmittance of 91%, a haze value of 16%, and a tensile modulus of 200 MPa, which were measured immediately after sterilization at 121° C. for 30 minutes.

Example 5

A sheet 5 with a total thickness of 200 μm, which consists of a surface layer with a thickness of 20 μm, an intermediate layer with a thickness of 140 μm, and a heat-sealable layer with a thickness of 40 μm, was prepared by multi-layer coextrusion from the following materials.
  Material for the surface layer: A composition composed of component (a) defined above and propylene homopolymer in a ratio of 9:1.
  Material for the intermediate layer: A composition composed of component (a) defined above and a metallocene plastomer ("Kernel" from Japan Polychems, Inc.) having a tensile modulus of 100 MPa in a ratio of 8:2.
  Material for the heat-sealable layer: A composition composed of component (a) defined above, component (b) defined above, and a styrene-based elastomer containing 10% styrene ("Hybrar" from Kuraray Co., Ltd.) in a ratio of 70:25:5.

The thus obtained sheet 5 was heat-sealed at 200° C. and 0.5 MPa for 4 seconds to form the peripheral sealed part and the port sealed part. Then it was heat-sealed at 165° C. and 0.2 MPa for 2 seconds to form the weakly sealed part that separates the inside of the container into two compartments. Thus there was obtained a compartmented container 5. It was found that the peripheral sealed part and the weakly sealed part of the compartmented container 5 have a seal strength of 32 N/15 mm and 2.5 N/15 mm, respectively. It was found that the weakly sealed part allows a margin of 40° C. for its heat-sealing temperature, which was measured in the same way as in Example 1.

The resulting compartmented container 5 having two compartments divided was evaluated as follows. Each of two compartments was filled with 1 liter of distilled water for injection and then sealed. The container underwent sterilization at 121° C. for 30 minutes. The weakly sealed part did not rupture after sterilization, and it was possible to join the compartments together easily by pressing with hand. The container was found to have a total light transmittance of 90%, a haze value of 16%, and a tensile modulus of 200 MPa, which were measured immediately after sterilization at 121° C. for 30 minutes.

Example 6

A multi-layer film 6 of four-layer structure was obtained by dry lamination from the following films.

The first layer (the outermost layer): polyethylene terephthalate film with a thickness of 12 μm ("Ester E5102" from Toyobo Co., Ltd.)

The second layer: alumina-deposited polyester terephthalate film with a thickness of 12 μm ("GL Film" from Toppan Printing Co., Ltd.)

The third layer: nylon film with a thickness of 15 μm with a thickness of "Emblem" from Unitika Co., Ltd.)

The fourth layer: a film with a thickness of 40 μm formed by inflation method from a composition composed of component (a) defined above and component (b) defined above in a ratio of 9:1.

The thus obtained multi-layer film 6 was heat-sealed at 200° C. and 0.5 MPa for 4 seconds to form the peripheral sealed part and the port sealed part. Then it was heat-sealed at 165° C. and 0.2 MPa for 2 seconds to form the weakly sealed part that separates the inside of the container into two compartments. Thus there was obtained a compartmented container 6. It was found that the peripheral sealed part and the weakly sealed part of the compartmented container 5 have a seal strength of 32 N/15 mm and 2.5 N/15 mm, respectively. It was found that the weakly sealed part allows a margin of 30° C. for its heat-sealing temperature, which was measured in the same way as in Example 1.

The resulting compartmented container 5 having two compartments divided was evaluated as follows. Each of two compartments was filled with 1 liter of distilled water for injection and then sealed. The container underwent sterilization at 121° C. for 30 minutes. The weakly sealed part did not rupture after sterilization, and it was possible to join the compartments together easily by pressing with hand to make two compartments communicate with each other. The container was found to have a total light transmittance of 90% and a haze value of 16% which were measured immediately after sterilization at 121° C. for 30 minutes.

Comparative Example 1

A sheet 1' with a total thickness of 200 μm, which consists of a surface layer with a thickness of 20 μm, an intermediate layer with a thickness of 140 μm, and a heat-sealable layer with a thickness of 40 μm, was prepared by multi-layer coextrusion from the following materials.

Material for the surface layer: A composition composed of component (a) defined above and propylene homopolymer in a ratio of 9:1.

Material for the intermediate layer: A composition composed of component (a) defined above and a metallocene plastomer ("Kernel" from Japan Polychems, Inc.) having a tensile modulus of 100 MPa in a ratio of 8:2.

Material for the heat-sealable layer: Component (a) defined above.

The thus obtained sheet 1' was heat-sealed at 200° C. and 0.5 MPa for 4 seconds to form the peripheral sealed part and the port sealed part. Then it was heat-sealed at 160° C. and 0.2 MPa for 2 seconds to form the weakly sealed part that separates the inside of the container into two compartments. Thus there was obtained a compartmented container 1'. It was found that the peripheral sealed part and the weakly sealed part of the compartmented container 1' have a seal strength of 30 N/15 mm and 2 N/15 mm, respectively. However, it was also found that the weakly sealed part allows a margin of only 20° C. for its heat-sealing temperature, which was too narrow for the compartmented container to be of practical use.

Comparative Example 2

The same procedure as in Comparative Example 1 was repeated to prepare a sheet 2' with a total thickness of 200 μm, which consists of a surface layer with a thickness of 20 μm, an intermediate layer with a thickness of 140 μm, and a heat-sealable layer with a thickness of 40 μm, except that the heat-sealable layer was formed from component (b) defined above.

The thus obtained sheet 2' was heat-sealed in the same way as in Comparative Example 1 to form the peripheral sealed part which separates the inside of the container into two compartments and the port sealed part. Thus there was obtained a compartmented container 2'. It was found that the peripheral sealed part of the compartmented container 2' have a seal strength of 30 N/15 mm; however, it was impossible to form the weakly sealed part on account of the excessively narrow latitude for heat sealing temperature.

The invention claimed is:

1. A compartmented container to hold two or more contents separately in individual compartments, which is formed from a resin film or sheet having a heat-sealable layer on at least one side thereof so that the heat-sealable layer constitutes the inner walls of said container, and the opposing inner walls are heat-sealed partially and peelably to form the weakly sealed part which divides the inside of the container into compartments, wherein said heat-sealable layer is formed from a composition of propylene copolymer composed of the following components (A) and (B), wherein Component (A): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 15 wt % and not more than 40 wt %, and the ratio of the amount of elution at 60° C. to 90° C. to the whole amount of elution is not less than 5 wt % and less than 15 wt %, Component (B): a propylene copolymer composed of propylene and ethylene and/or $C_{4-8}$ α-olefin, which gives such a specific ratio of the amount of elution measured by the temperature rising elution fractionation method (at temperatures ranging from 0° C. to 140° C. with o-dichlorobenzene as a solvent) that the ratio of the amount of elution at 0° C. to the whole amount of elution is not less than 2 wt % and not more than 15 wt %, and the ratio of the amount of elution at 60° C. to 90° C. to the whole amount of elution is not less than 20 wt % and not more than 60 wt %.

2. The compartmented container as defined in claim 1, wherein the weakly sealed part is formed by heat-sealing with an easy peel tape inserted between the opposing inner walls, said tape having as the surface layer a heat-sealable layer composed of said composition of propylene copolymer.

3. The compartmented container as defined in claim 1 or 2, which has a port made from polypropylene resin.

4. The compartmented container as defined in claim 1, wherein the composition of propylene copolymers is composed of component (A) and component (B) in a ratio of from 98:2 to 50:50 (by weight).

5. The compartmented container as defined in claim 1, wherein the composition of propylene copolymers contains a styrene elastomer with a styrene content not more than 25 wt % in an amount of 1 to 10 wt %.

6. The compartmented container as defined in claim 1, wherein the resin film or sheet has a laminated structure of at least three layers, including heat-sealable layer, intermediate layer, and the outermost layer.

7. The compartmented container as defined in claim 1, wherein the resin film or sheet gives a total light transmittance not lower than 80% and a haze value not higher than 25% when tested according to JIS K7105 immediately after sterilization at 121° C. for 30 minutes.

8. The compartmented container as defined in claim 1, wherein the weakly sealed part gives a heat seal strength of 1 to 6 N/15 mm and the other heat-sealed part than the weakly sealed part gives a heat seal strength not lower than 25 N/15 mm when tested according to JIS Z0238 (for 180° peeling).

9. The compartmented container as defined in claim 8, wherein the capacity is smaller than 500 mL, and the weakly sealed part has a heat seal strength of 1 to 3 N/15 mm.

10. The compartmented container as defined in claim 8, wherein the capacity is not smaller than 500 mL, and the weakly sealed part has a heat seal strength of 3 to 6 N/15 mm.

* * * * *